United States Patent [19]
Holtzman

[11] Patent Number: 5,969,123
[45] Date of Patent: Oct. 19, 1999

[54] NUCLEIC ACID MOLECULES DERIVED FROM A BRAIN TISSUE LIBRARY

[75] Inventor: Douglas A. Holtzman, Cambridge, Mass.

[73] Assignee: Millennium Biotherapeutics, Inc., Cambridge, Mass.

[21] Appl. No.: 09/036,089

[22] Filed: Mar. 6, 1998

[51] Int. Cl.$^6$ .............................. C07H 21/02; C07H 21/04
[52] U.S. Cl. .......................................... 536/23.1; 536/22.1
[58] Field of Search ..................................... 536/22.1, 23.1

[56] References Cited

PUBLICATIONS

Sakurai et al., "Orexins and Orexin Receptors: A Family of Hypothalamic Neuropeptides and G Protein–Coupled Receptors that Regulate Feeding Behavior", *Cell*, 92:573–585 (1998).

deLecea et al., "The Hypocretins: Hypothalamus–Specific Peptides with Neuroexcitatory Activity", *Proc. Natl. Acad. Sci. USA*, 95(1):322–327 (1998).

*Primary Examiner*—Eggerton A. Campbell
*Attorney, Agent, or Firm*—Hamilton, Brook, Smith & Reynolds, P.C.

[57] ABSTRACT

The invention provides nucleic acid molecules derived from a brain tissue library. The nucleic acid molecules are used in applications such as diagnostic methods, screening assays and as hybridization probes and primers.

16 Claims, 2 Drawing Sheets

> jtmba218f09t1    (SEQ ID NO: 1)

GACCACGCCTCCGCCCACGCGTCCGGACTTCTTGGGTATTTGGACCACTGCACTGAAG
AGATCATCTCTCCAGATTACTTTCCCCTGAGCTCCAGGCACCATGAACTTTCCTTCTA
CAAAGGTTCCCTGGGCCGCCGTGACGCTGCTGCTGCTGCTACTGCTGCCGCCGGCGCT
GCTGTCGCTTGGGGTGGACGCACAGCCTCTGCCCGACTGCTGTCGCCAGAAGACGTGT
TCCTGCCGTCTCTACGAACTGTTGCACGGAGCTGGCAACCACGCTGCGGGTATCCTGA
CTCTGGGAAAGCGGCGGCCTGGACCTCCAGGCCTCCAAGGGACGCTGCAGCGCCTCCTTC

>jtmba218f09t1    (SEQ ID NO: 2)

GACCACGCCTCCGCCCACGCGTCCGGACTTCTTGGGTATTTGGACCACTGCACTGAAG
AGATCATCTCTCCAGATTACTTTCCCCTGAGCTCCAGGCACCATGAACTTTCCTTCTA
CAAAGGTTCCCTGGGCCGCCGTGACGCTGCTGCTGCTGCTACTGCTGCCGCCGGCGCT
GCTGTCGCTTGGGGTGGACGCACAGCCTCTGCCCGACTGCTGTCGCCAGAAGACGTGT
TCCTGCCGTCTCTACGAACTGTTGCACGGAGCTGGCAACCACGCTGCGGGTATCCTGA
CTCTGGGAAAGCGGCGGCCTGGACCTCCAGGCCTCCAGGGACGGCTGCAGCGCCTCCTTC

> jamha074h05m2    (SEQ ID NO: 3)

GCACGAGGCCGCCGTGACGCTGCTGCTGCTGCTACTGCTGCCGCCGGCGCTGCTGTCG
CTTGGGGTGGGACGCACAGTCTCTGCCCGACTGCTGTCGCCAGAAGACGTGTTCCTGC
CGTCTCTACNAACTGTTGCACGGAGCTGGCAACCACGCTTGCNGGTATCCTGACTCTG
GNGAAAGCGGCGGTCTGGACCTCCAGGCCTTCAGGGACGGCTGCAGCGCCTNCTTCAG
GCCAACGGTAACCACGCAGCTGGCATC

>jamha074h05m2    (SEQ ID NO: 4)

GCCGCCGTGACGCTGCTGCTGCTGCTACTGCTGCCGCCGGCGCTGCTGTCGCTTGGGG
TGGACGCACAGCCTCTGCCCGACTGCTGTCGCCAGAAGACGTGTTCCTGCCGTCTCTA
CNAACTGTTGCACGGAGCTGGCAACCACGCTGCGGGTATCCTGACTCTGGGAAAGCGG
CGGNCTGGACCTCCAGGCCTTCAGGGACGGCTGCAGCGCCTNCTTCAGGCCAACGGTA
ACCACGCAGCTGGCATCCTGACCATGGGCCGCCGTGCAGGCNGCANAGCTAGAGCCAC
ATCCCTGA

FIG. 1

>contiguous sequence (SEQ ID NO: 5)

```
GACCACGCCTCCGCCCACGCGTCCGGACTTCTTGGGTATTTGGACCACTGCACTGAAG
AGATCATCTCTCCAGATTACTTTCCCCTGAGCTCCAGGCACCATGAACTTTCCTTCTA
CAAAGGTTCCCTGGGCCGCCGTGACGCTGCTGCTGCTGCTACTGCTGCCGCCGGCGCT
GCTGTCGCTTGGGGTGGACGCACAGCCTCTGCCCGACTGCTGTCGCCAGAAGACGTGT
TCCTGCCGTCTCTACGAACTGTTGCACGGAGCTGGCAACCACGCTGCGGGTATCCTGA
CTCTGGGAAAGCGGCGGCCTGGACCTCCAGGCCTYCAGGGACGGCTGCAGCGCCTCCT
TCAGGCCAACGGTAACCACGCAGCTGGCATCCTGACCATGGGCCGCCGTGCAGGCNGC
ANAGCTAGAGCCACATCCCTGA
```

FIG. 2

```
                          SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
          (A) LENGTH: 350 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:1:

GACCACGCCT CCGCCCACGC GTCCGGACTT CTTGGGTATT TGGACCACTG CACTGAAGAG      60

ATCATCTCTC CAGATTACTT TCCCCTGAGC TCCAGGCACC ATGAACTTTC CTTCTACAAA     120

GGTTCCCTGG GCCGCCGTGA CGCTGCTGCT GCTGCTACTG CTGCCGCCGG CGCTGCTGTC     180

GCTTGGGGTG GACGCACAGC CTCTGCCCGA CTGCTGTCGC CAGAAGACGT GTTCCTGCCG     240

TCTCTACGAA CTGTTGCACG GAGCTGGCAA CCACGCTGCG GGTATCCTGA CTCTGGGAAA     300

GCGGCGGCCT GGACCTCCAG GCCTCCAAGG GACGCTGCAG CGCCTCCTTC                350

(2) INFORMATION FOR SEQ ID NO:2:

(i) SEQUENCE CHARACTERISTICS:
          (A) LENGTH: 350 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:2:

GACCACGCCT CCGCCCACGC GTCCGGACTT CTTGGGTATT TGGACCACTG CACTGAAGAG      60

ATCATCTCTC CAGATTACTT TCCCCTGAGC TCCAGGCACC ATGAACTTTC CTTCTACAAA     120

GGTTCCCTGG GCCGCCGTGA CGCTGCTGCT GCTGCTACTG CTGCCGCCGG CGCTGCTGTC     180

GCTTGGGGTG GACGCACAGC CTCTGCCCGA CTGCTGTCGC CAGAAGACGT GTTCCTGCCG     240

TCTCTACGAA CTGTTGCACG GAGCTGGCAA CCACGCTGCG GGTATCCTGA CTCTGGGAAA     300

GCGGCGGCCT GGACCTCCAG GCCTCCAGGG ACGGCTGCAG CGCCTCCTTC                350

(2) INFORMATION FOR SEQ ID NO:3:

(i) SEQUENCE CHARACTERISTICS:
          (A) LENGTH: 259 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:3:

GCACGAGGCC GCCGTGACGC TGCTGCTGCT GCTACTGCTG CCGCCGGCGC TGCTGTCGCT      60
```

-continued

```
TGGGGTGGGA CGCACAGTCT CTGCCCGACT GCTGTCGCCA GAAGACGTGT TCCTGCCGTC      120

TCTACNAACT GTTGCACGGA GCTGGCAACC ACGCTTGCNG GTATCCTGAC TCTGGNGAAA      180

GCGGCGGTCT GGACCTCCAG GCCTTCAGGG ACGGCTGCAG CGCCTNCTTC AGGCCAACGG      240

TAACCACGCA GCTGGCATC                                                  259
```

(2) INFORMATION FOR SEQ ID NO:4:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

```
GCCGCCGTGA CGCTGCTGCT GCTGCTACTG CTGCCGCCGG CGCTGCTGTC GCTTGGGGTG       60

GACGCACAGC CTCTGCCCGA CTGCTGTCGC CAGAAGACGT GTTCCTGCCG TCTCTACNAA      120

CTGTTGCACG GAGCTGGCAA CCACGCTGCG GGTATCCTGA CTCTGGGAAA GCGGCGGNCT      180

GGACCTCCAG GCCTTCAGGG ACGGCTGCAG CGCCTNCTTC AGGCCAACGG TAACCACGCA      240

GCTGGCATCC TGACCATGGG CCGCCGTGCA GGCNGCANAG CTAGAGCCAC ATCCCTGA       298
```

(2) INFORMATION FOR SEQ ID NO:5:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

```
GACCACGCCT CCGCCCACGC GTCCGGACTT CTTGGGTATT TGGACCACTG CACTGAAGAG       60

ATCATCTCTC CAGATTACTT TCCCCTGAGC TCCAGGCACC ATGAACTTTC CTTCTACAAA      120

GGTTCCCTGG GCCGCCGTGA CGCTGCTGCT GCTGCTACTG CTGCCGCCGG CGCTGCTGTC      180

GCTTGGGGTG GACGCACAGC CTCTGCCCGA CTGCTGTCGC CAGAAGACGT GTTCCTGCCG      240

TCTCTACGAA CTGTTGCACG GAGCTGGCAA CCACGCTGCG GGTATCCTGA CTCTGGGAAA      300

GCGGCGGCCT GGACCTCCAG GCCTYCAGGG ACGGCTGCAG CGCCTCCTTC AGGCCAACGG      360

TAACCACGCA GCTGGCATCC TGACCATGGG CCGCCGTGCA GGCNGCANAG CTAGAGCCAC      420

ATCCCTGA                                                              428
```

NUCLEIC ACID MOLECULES DERIVED FROM A BRAIN TISSUE LIBRARY

BACKGROUND OF THE INVENTION

Many behavioral and physiological disorders may have their cause(s) rooted in abnormal gene expression in the brain. Thus, diagnostic and therapeutic approaches to many neuronal disorders can benefit from a better understanding of the characterization and expression of genes in the brain.

SUMMARY OF THE INVENTION

The present invention relates to the identification of novel nucleic acid molecules isolated from a brain tissue library. In one embodiment, the nucleic acid molecules comprise a nucleotide sequence selected from the group consisting of SEQ ID NOS: 1–5 and the complement of SEQ ID NOS: 1–5. In another embodiment, the nucleic acid molecule hybridizes under high stringency conditions to a nucleotide sequence selected from the group consisting of SEQ ID NOS: 1–5 and the complement of SEQ ID NOS: 1–5. In a further embodiment, the nucleic acid molecule of the invention comprises a nucleotide sequence which is greater than about 75 percent, and more preferably greater than about 80 percent, and even more preferably greater than about 90 percent, identical to a nucleotide sequence selected from the group consisting of SEQ ID NOS: 1–5 and the complement of SEQ ID NOS: 1–5.

The invention also relates to an isolated nucleic acid molecule consisting of a nucleotide sequence selected from the group consisting of SEQ ID NOS: 1–5 and the complement of SEQ ID NOS: 1–5. The invention further relates to an isolated portion of any of SEQ ID NOS: 1–5 and the complement of SEQ ID NOS: 1–5, which portion is sufficient in length to distinctly characterize the sequence. For example, the isolated portion can be from about 7 to about 15 nucleotides in length, and more preferably from about 15 to about 25 nucleotides in length.

The invention further relates to isolated proteins and polypeptides encoded by nucleic acid molecules of the invention. The invention also pertains to antibodies, including monoclonal antibodies, or antigen-binding fragments thereof, which selectively bind to the isolated proteins and polypeptides of the invention.

The invention also relates to DNA constructs comprising the nucleic acid molecules described above operatively linked to a regulatory sequence, and to recombinant host cells, such as bacterial cells, fungal cells, plant cells, insect cells and mammalian cells, comprising the nucleic acid molecules described above operatively linked to a regulatory sequence. The invention further relates to methods for preparing proteins and polypeptides encoded by isolated nucleic acid molecules described herein, comprising culturing a recombinant host cell described herein comprising an isolated nucleic acid molecule of the invention operatively linked to a regulatory sequence.

The invention also relates to a method for assaying the presence of a protein or polypeptide encoded by a nucleic acid molecule of the present invention, in a sample, e.g., in a tissue sample, comprising contacting said sample with an antibody which specifically binds to the encoded protein or polypeptide.

The invention also pertains to a method for assaying the present of a nucleic acid molecule comprising a nucleotide sequence selected from the group consisting of SEQ ID NOS: 1–5 and the complement of SEQ ID NOS: 1–5, in a sample, comprising contacting said sample with a nucleotide sequence selected from the group consisting of SEQ ID NOS: 1–5, the complement of SEQ ID NOS: 1–5, and a portion of any one of SEQ ID NOS: 1–5 or the complement of SEQ ID NOS: 1–5 which is at least about 7 to about 15 nucleotides in length, and more preferably at least about 15 to about 25 nucleotides in length, under conditions appropriate for specific hybridization.

BRIEF DESCRIPTION OF THE DRAWINGS

FIG. 1 illustrate the nucleotide sequences (SEQ ID NOS: 1–4) of nucleic acid molecules derived from a mouse brain tissue library.

FIG. 2 illustrates the nucleotide sequence (SEQ ID NO: 5) of a contiguous nucleic acid molecule assembled from SEQ ID NOS: 1 and 3. Nucleotides 1–350 are derived from SEQ ID NO: 1, and nucleotides 131–428 are derived from SEQ ID NO: 3.

DETAILED DESCRIPTION OF THE INVENTION

As described herein, novel nucleic acid molecules have been identified from a brain tissue cDNA library. These nucleic acid molecules, or a subset thereof, can serve as markers to identify and characterize brain tissue. In one embodiment, the nucleic acid molecules comprise a nucleotide sequence selected from the group consisting of SEQ ID NOS: 1–5 and the complement of SEQ ID NOS: 1–5. In another embodiment, the nucleic acid molecule hybridizes under high stringency conditions to a nucleotide sequence selected from the group consisting of SEQ ID NOS: 1–5 and the complement of SEQ ID NOS: 1–5. In a further embodiment, the nucleic acid molecule of the invention comprises a nucleotide sequence which is greater than about 75 percent, and more preferably greater than about 80 percent, and even more preferably greater than about 90 percent, identical to a nucleotide sequence selected from the group consisting of SEQ ID NOS: 1–5 and the complement of SEQ ID NOS: 1–5. In a preferred embodiment, the nucleic acid molecule which hybridizes under conditions of high stringency to a nucleotide sequence selected from the group consisting of SEQ ID NOS: 1–5 is isolated from human tissue.

The invention also relates to an isolated nucleic acid molecule consisting of a nucleotide sequence selected from the group consisting of SEQ ID NOS: 1–5 and the complement of SEQ ID NOS: 1–5. The invention further relates to an isolated portion of any of SEQ ID NOS: 1–5 and the complement of SEQ ID NOS: 1–5, which portion is sufficient in length to distinctly characterize the sequence. For example, the isolated portion can be from about 7 to about 15 nucleotides in length, nucleotides in length, and more preferably from about 15 to about 25 nucleotides in length.

As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. Preferably, the nucleic acid molecule comprises at least about 10 nucleotides, more preferably at least about 50 nucleotides, and even more preferably at least about 200 nucleotides. The nucleic acid molecule can include all or a portion of the coding sequence of a gene and can further comprise additional non-coding sequences such as introns and non-coding 3' and 5' sequences (including regulatory sequences, for example).

Additionally, the nucleic acid molecule can be fused to a marker sequence, for example, a sequence which encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from influenza.

As used herein, an "isolated" gene or nucleic acid molecule is intended to mean a gene or nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Thus, recombinant DNA contained in a vector are included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded protein, as probes for isolating homologous sequences (e.g., from other mammalian species), for gene mapping (e.g., by in situ hybridization with chromosomes), or for detecting expression of the gene in tissue (e.g., human tissue such as brain tissue), such as by Northern blot analysis.

The invention described herein also relates to fragments or portions of the isolated nucleic acid molecules described above. The term "fragment" is intended to encompass a portion of a nucleic acid molecule described herein which is from at least about 7 contiguous nucleotides to at least about 25 contiguous nucleotides or longer in length; such fragments are useful as probes, e.g., for diagnostic methods and also as primers. Particularly preferred primers and probes selectively hybridize to nucleic acid molecules comprising the nucleotide sequences of any of SEQ ID NOS: 1–5 and the complement of SEQ ID NOS: 1–5. For example, fragments which encode antigenic proteins or polypeptides described herein are useful.

The invention also pertains to nucleic acid molecules which hybridize under high stringency hybridization conditions (e.g., for selective hybridization) to a nucleotide sequence described herein. Hybridization probes are oligonucleotides which bind in a base-specific manner to a complementary strand of nucleic acid. Such probes include polypeptide nucleic acids, as described in Nielsen et al., Science 254, 1497–1500 (1991). Appropriate stringency conditions are known to those skilled in the art or can be found in standard texts such as Current Protocols in Molecular Biology, John Wiley & Sons, N.Y. (1989), 6.3.1–6.3.6. For example, stringent hybridization conditions include a salt concentration of no more than 1M and a temperature of at least 25° C. In one embodiment, conditions of 5X SSPE (750 mM NaCl, 50 mM NaPhosphate, 5 mM EDTA, pH 7.4) and a temperature of 25–30° C., or equivalent conditions, are suitable for specific probe hybridizations. Equivalent conditions can be determined by varying one or more of the parameters given as an example, as known in the art, while maintaining a similar degree of identity or similarity between the target nucleic acid molecule and the primer or probe used. Hybridizable nucleic acid molecules are useful as probes and primers for diagnostic applications.

As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

Accordingly, the invention pertains to nucleic acid molecules which have a substantial identity with the nucleic acid molecules described herein; particularly preferred are nucleic acid molecules which have at least about 90%, and more preferably at least about 95% identity with nucleic acid molecules described herein. Thus, DNA molecules which comprise a sequence which is different from the naturally-occurring nucleic acid molecule but which, due to the degeneracy of the genetic code, encode the same protein or polypeptide are the subject of this invention. The invention also encompasses variations of the nucleic acid molecules of the invention, such as those encoding portions, analogues or derivatives of the encoded protein or polypeptide. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent; that is, they do not alter the characteristics or activity of the encoded protein or polypeptide. As used herein, activities of the encoded protein or polypeptide include, but are not limited to, catalytic activity, binding function, antigenic function and oligomerization function.

The nucleotide sequences of the nucleic acid molecules described herein, e.g., SEQ ID NOS: 1–5 and the complement of SEQ ID NOS: 1–5, can be amplified by methods known in the art. For example, this can be accomplished by e.g., PCR. See generally *PCR Technology: Principles and Applications for DNA Amplification* (ed. H. A. Erlich, Freeman Press, NY, N.Y., 1992); PCR Protocols: *A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a cDNA library derived from brain tissue, e.g., human brain tissue, mRNA in λzap express, ZIPLOX or other suitable vector. Corresponding clones can be isolated, DNA can obtained following in vivo excision, and the cloned insert can be sequenced in either or both orientations by art recognized methods, to identify the correct reading frame encoding a protein of the appropriate molecular weight. For example, the direct analysis of the nucleotide sequence of nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein(s) and the DNA encoding the protein can be isolated, sequenced and further characterized.

With respect to protein or polypeptide identification, bands identified by gel analysis can be isolated and purified by HPLC, and the resulting purified protein can be sequenced. Alternatively, the purified protein can be enzymatically digested by methods known in the art to produce polypeptide fragments which can be sequenced. The sequencing can be performed, for example, by the methods of Wilm et al. (*Nature* 379(6564):466–469 (1996)). The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); *Scopes, Protein Purification, Principles and Practice*, 2nd Edition, Springer-Verlag, New York (1987); and Deutscher (ed), Guide to Protein Purification, *Methods in Enzymology*, Vol. 182 (1990). If the protein is secreted, it can be isolated from the supernatant in which the host cell is grown. If not secreted, the protein can be isolated from a lysate of the host cells.

In addition to substantially full-length polypeptides encoded by nucleic acid molecules described herein, the present invention includes biologically active fragments of the polypeptides, or analogs thereof, including organic molecules which simulate the interactions of the polypeptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

This invention also pertains to an isolated protein or polypeptide encoded by the nucleic acid molecules of the invention. The encoded proteins or polypeptides of the invention can be partially or substantially purified (e.g., purified to homogeneity), and/or are substantially free of other proteins. According to the invention, the amino acid sequence of the polypeptide can be that of the naturally-occurring protein or can comprise alterations therein. Such alterations include conservative or non-conservative amino acid substitutions, additions and deletions of one or more amino acids; however, such alterations should preserve at least one activity of the encoded protein or polypeptide, i.e., the altered or mutant protein should be an active derivative of the naturally-occurring protein. For example, the mutation(s) can preferably preserve the three dimensional configuration of the binding and/or catalytic site of the native protein. The presence or absence of biological activity or activities can be determined by various functional assays as described herein. Moreover, amino acids which are essential for the function of the encoded protein or polypeptide can be identified by methods known in the art. Particularly useful methods include identification of conserved amino acids in the family or subfamily, site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310 (1990)).

The encoded polypeptide can also be a fusion protein comprising all or a portion of the amino acid sequence fused to an additional component. Additional components, such as radioisotopes and antigenic tags, can be selected to assist in the isolation or purification of the polypeptide or to extend the half life of the polypeptide; for example, a hexahistidine tag would permit ready purification by nickel chromatography. Furthermore, polypeptides of the present invention can be progenitors of the active protein; progenitors are molecules which are cleaved to form an active molecule.

Polypeptides described herein can be isolated from naturally-occurring sources, chemically synthesized or recombinantly produced. Polypeptides or proteins of the present invention can be used as a molecular weight marker on SDS-PAGE gels or on molecular sieve gel filtration columns using art-recognized methods.

The invention also provides expression vectors containing a nucleic acid sequence described herein, operably linked to at least one regulatory sequence. Many such vectors are commercially available, and other suitable vectors can be readily prepared by the skilled artisan. "Operably linked" is intended to meant that the nucleic acid molecule is linked to a regulatory sequence in a manner which allows expression of the nucleic acid sequence. Regulatory sequences are art-recognized and are selected to produce the encoded polypeptide or protein. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression,* ed. M. Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains, Streptomyces, Pseudomonas, *Serratia marcescens* and *Salmonella typhimurium,* insect cells (baculovirus), including Drosophila, fungal cells, such as yeast cells, plant cells and mammalian cells, such as thymocytes, Chinese hamster ovary cells (CHO), and COS cells.

Thus, a nucleic acid molecule described herein can be used to produce a recombinant form of the protein via microbial or eukaryotic cellular processes. Ligating the polynucleic acid molecule into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of encoded proteins or polypeptides by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind a polypeptide or protein of the invention. For instance, polyclonal and monoclonal antibodies, including non-human and human antibodies, humanized antibodies, chimeric antibodies and antigen-binding fragments thereof (Current Protocols in Immunology, John Wiley & Sons, N.Y. (1994); EP Application 173,494 (Morrison); International Patent Application W086/01533 (Neuberger); and U.S. Pat. No. 5,225,539 (Winters)) which bind to the described protein or polypeptide are within the scope of the invention. A mammal, such as a mouse, rat, hamster or rabbit, can be immunized with an immunogenic form of the protein (e.g., the full length protein or a polypeptide comprising an antigenic fragment of the protein which is capable of eliciting an antibody response). Techniques for conferring immunogenicity on a protein or polypeptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, Nature 256:495–497 (1975); Kozbar et al., *Immunology Today* 4:72 (1983); and Cole et al., *Monoclonal Antibodies and Cancer Therapy,* Alan R. Liss, Inc., pp. 77–96 (1985)). The term "antibody" as used herein is intended to include fragments thereof, such as Fab and F(ab)$_2$. Antibodies described herein can be used to inhibit the activity of the polypeptides and proteins described herein, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the protein or polypeptide. Tissue samples which can be assayed include human tissues, e.g., differentiated and non-differentiated cells. Examples include bone marrow, thymus, kidney, liver, brain, pancreas, fibroblasts and epithelium. These antibodies are useful in diagnostic assays, or as an active ingredient in a pharmaceutical composition.

The present invention also pertains to pharmaceutical compositions comprising polypeptides and other compounds described herein. For instance, a polypeptide or protein, or prodrug thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices and slow release polymeric devices. The pharmaceutical compositions of this invention can also be administered as part of a combinatorial therapy with other agents.

The invention further provides kits comprising at least all or a portion of the nucleic acid molecules as described herein. Often, the kits contain one or more pairs of oligonucleotides which hybridize to a particular nucleotide sequence. In some kits, the oligonucleotides are provided immobilized to a substrate. For example, the same substrate can comprise oligonucleotide probes for detecting at least 10, 100 or more nucleic acid sequences. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

A. Screening Assays:

The invention provides a method (also referred to herein as a "screening assay") for identifying modulators, i.e., candidate or test compounds or agents (e.g., antisense, polypeptides, peptidomimetics, small molecules or other drugs) which bind to nucleic acid molecules, polypeptides or proteins described herein or have a stimulatory or inhibitory effect on, for example, expression or activity of the nucleic acid molecules, polypeptides or proteins of the invention.

In one embodiment, the invention provides assays for screening candidate or test compounds which bind to or modulate the activity of protein or polypeptide described herein or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. U.S.A.,* 90:6909; Erb et al. (1994) *Proc. Natl. Acad. Sci. U.S.A.,* 91:11422; Zuckermann et al. (1994). *J. Med. Chem.,* 37:2678; Cho et al. (1993) *Science,* 261:1303; Carell et al. (1994) Angew. *Chem. Int. Ed. Engl.,* 33:2059; Carell et al. (1994) Angew. *Chem. Int. Ed. Engl.,* 33:2061; and in Gallop et al. (1994) *J. Med. Chem.,* 37:1233.

Libraries of compounds may be presented in solution (e.g., Houghten(1992)Biotechniques, 13:412–421), or on beads (Lam(1991) *Nature,* 354:82–84), chips (Fodor (1993) *Nature,* 364;555–556), bacteria(Ladner U.S. Pat. No. 5,223, 409), spores (Ladner U.S. Pat. No. '409), plasmids (Cull et al.(1992) *Proc. Natl. Acad. Sci. U.S.A.,* 89:1865–1869) or on phage (Scott and Smith (1990) *Science,* 249:386–390); (Devlin (1990) *Science,* 249:404–406); (Cwirla et al. (1990) *Proc. Natl. Acad. Sci.,* 97:6378–6382); (Felici (1991) *J. Mol. Biol.,* 222:301–310); (Ladner supra).

In one embodiment, an assay is a cell-based assay in which a cell which expresses an encoded protein which is a cell surface receptor is contacted with a test compound and the ability of the test compound to bind to the receptor is determined. The cell, for example, can be of mammalian origin, such as from a neuron or brain cell. Determining the ability of the test compound to bind to the receptor can be accomplished, for example, by coupling the test compound with a radioisotope or enzymatic label such that binding of the test compound to the receptor can be determined by detecting the labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a test compound to interact with the receptor without the labeling of any of the interactants. For example, a microphysiometer can be used to detect the interaction of a test compound with the receptor without the labeling of either the test compound or the receptor. McConnell, H. M. et al. (1992) *Science,* 257:1906–1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and receptor.

In one embodiment, the assay comprises contacting a cell which expresses an encoded protein described herein on the cell surface (e.g., a receptor) with a receptor ligand or biologically-active portion thereof, to form an assay mixture, contacting the assay mixture with a test compound, and determining the ability of the test compound to interact with the receptor, wherein determining the ability of the test compound to interact with the receptor comprises determining the ability of the test compound to preferentially bind to the receptor as compared to the ability of the ligand, or a biologically active portion thereof, to bind to the receptor.

In another embodiment, an assay is a cell-based assay comprising contacting a cell expressing a particular target molecule described herein with a test compound and determining the ability of the test compound to modulate or alter (e.g. stimulate or inhibit) the activity of the target molecule. Determining the ability of the test compound to modulate the activity of the target molecule can be accomplished, for example, by determining the ability of a known ligand to bind to or interact with the target molecule.

Determining the ability of the known ligand to bind to or interact with the target molecule can be accomplished by one of the methods described above for determining direct binding. In a preferred embodiment, determining the ability of the known ligand to bind to or interact with the target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a cellular response, for example, development, differentiation or rate of proliferation.

In yet another embodiment, an assay of the present invention is a cell-free assay in which protein of the invention or biologically active portion thereof is contacted with a test compound and the ability of the test compound to bind to the protein or biologically active portion thereof is determined. Binding of the test compound to the protein can be determined either directly or indirectly as described above. In one embodiment, the assay includes contacting the protein or biologically active portion thereof with a known compound which binds the protein to form an assay mixture, contacting the assay mixture with a test compound, and determining the ability of the test compound to interact with the protein. Determining the ability of the test compound to interact with the protein comprises determining the ability of the test compound to preferentially bind to the protein or biologically active portion thereof as compared to the known compound.

In another embodiment, the assay is a cell-free assay in which a protein of the invention or biologically active portion thereof is contacted with a test compound and the ability of the test compound to modulate or alter (e.g., stimulate or inhibit) the activity of the protein or biologically active portion thereof is determined. Determining the ability of the test compound to modulate the activity of the protein can be accomplished, for example, by determining the ability of the protein to bind to a known target molecule by one of the methods described above for determining direct binding. Determining the ability of the protein to bind to a target molecule can also be accomplished using a technology such as real-time Bimolecular Interaction Analysis (BIA). Sjolander, S. and Urbaniczky, C. (1991) *Anal. Chem.,* 63:2338–2345 and Szabo et al. (1995) *Curr. Opin. Struct. Biol.,* 5:699–705. As used herein, "BIA" is a technology for studying biospecific interactions in real time, without labeling any of the interactants (e.g., BIAcore™) . Changes in the optical phenomenon surface plasmon resonance (SPR) can be used as an indication of real-time reactions between biological molecules.

In an alternative embodiment, determining the ability of the test compound to modulate the activity of a protein of the invention can be accomplished by determining the ability of the protein to further modulate the activity of a target molecule. For example, the catalytic/enzymatic activity of the target molecule on an appropriate substrate can be determined as previously described.

In yet another embodiment, the cell-free assay involves contacting a protein of the invention or biologically active portion thereof with a known compound which binds the protein to form an assay mixture, contacting the assay mixture with a test compound, and determining the ability of the test compound to interact with the protein, wherein determining the ability of the test compound to interact with the protein comprises determining the ability of the protein to preferentially bind to or modulate the activity of a target molecule.

The cell-free assays of the present invention are amenable to use of both soluble and/or membrane-bound forms of isolated proteins. In the case of cell-free assays in which a membrane-bound form an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton®X-100, Triton®X-114, Thesit®, Isotridecypoly (ethylene glycol ether)$_n$,3-[(3-cholamidopropyl) dimethylamminio]-1-propane sulfonate (CHAPS), 3-[(3-cholamidopropyl)dimethylamminio]2-hydroxy-1-propane sulfonate (CHAPSO), or N-dodecyl-N,Ndimethyl-3-ammonio-1-propane sulfonate.

In more than one embodiment of the above assay methods of the present invention, it may be desirable to immobilize either the protein or its target molecule to facilitate separation of complexed from uncomplexed forms of one or both of the proteins, as well as to accommodate automation of the assay. Binding of a test compound to the protein, or interaction of the protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or protein of the invention, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either a protein of the invention or a target molecule can be immobilized utilizing conjugation of biotin and streptavidin. Biotinylated protein of the invention or target molecules can be prepared from biotin-NHS(N-hydroxysuccinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a protein of the invention or target molecules, but which do not interfere with binding of the protein to its target molecule, can be derivatized to the wells of the plate, and unbound target or protein trapped in the wells by antibody conjugation. Methods for detecting such complexes, in addition to those described above for the GST-immobilized complexes, include immunodetection of complexes using antibodies reactive with the protein or target molecule, as well as enzyme-linked assays which rely on detecting an enzymatic activity associated with the protein or target molecule.

In another embodiment, modulators of expression of nucleic acid molecules of the invention are identified in a method wherein a cell is contacted with a candidate compound and the expression of appropriate mRNA or protein in the cell is determined. The level of expression of appropriate mRNA or protein in the presence of the candidate compound is compared to the level of expression of mRNA or protein in the absence of the candidate compound. The candidate compound can then be identified as a modulator of expression based on this comparison. For example, when expression of mRNA or protein is greater (statistically significantly greater) in the presence of the candidate compound than in its absence, the candidate compound is identified as a stimulator or enhancer of the mRNA or protein expression. Alternatively, when expression of the mRNA or protein is less (statistically significantly less) in the presence of the candidate compound than in its absence, the candidate compound is identified as an inhibitor of the mRNA or protein expression. The level of mRNA or protein expression in the cells can be determined by methods described herein for detecting mRNA or protein.

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell,* 72:223–232; Madura et al. (1993) *J. Biol. Chem.,* 268:12046–12054; Bartel et al. (1993) *Biotechniques,* 14:920–924; Iwabuchi et al. (1993) *Oncogene,* 8:1693–1696; and Brent WO94/10300), to identify other proteins (captured proteins) which bind to or interact with the proteins of the invention and modulate their activity. Such captured proteins are also likely to be involved in the propagation of signals by the proteins of the invention as, for example, downstream elements of a protein-mediated signaling pathway. Alternatively, such captured proteins are likely to be cell-surface molecules associated with non-protein-expressing cells, wherein such captured proteins are involved in signal transduction.

The two-hybrid system is based on the modular nature of most transcription factors, which consist of separable DNA-binding and activation domains. Briefly, the assay utilizes two different DNA constructs. In one construct, the gene that codes for a protein of the invention is fused to a gene encoding the DNA binding domain of a known transcription factor (e.g., GAL-4) . In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected, and cell colonies containing the functional transcription factor can be isolated and used to obtain the cloned gene which encodes the protein which interacts with the protein of the invention.

This invention further pertains to novel agents identified by the above-described screening assays. Accordingly, it is within the scope of this invention to further use an agent identified as described herein in an appropriate animal model. For example, an agent identified as described herein (e.g., a modulating agent, an antisense nucleic acid molecule, a specific antibody, or a protein-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the nucleotide sequences identified herein (and the corresponding complete gene sequences) can be used in numerous ways as polynucleotide reagents. For example, these sequences can be used to: (I) map their respective genes on a chromosome; and, thus, locate gene regions associated with genetic disease; (ii) identify an individual from a minute biological sample (tissue typing); and (iii) aid in forensic identification of a biological sample. These applications are described in the subsection below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the nucleic acid molecules, described herein, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 bp in length) from the nucleic acid molecules described herein. Computer analysis of the sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the appropriate nucleotide sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science,* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the nucleic acid molecules of the invention to design oligonucleotide primers, sublocalization can be achieved with panels of fragments from specific chromosomes. Other mapping strategies which can similarly be used to map a specified sequence to its chromosome include in situ hybridization (described in Fan, Y et al. (1990) *PNAS,* 97:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. for a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Medelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J et al. (1987) *Nature,* 325:783–787.

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible form chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The nucleotide sequences of the present invention can also be used to identify individuals from minute biological samples, such as for brain tissue typing. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid molecules described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid molecules of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of these sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from nucleic acid molecules described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means of positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of sequences described herein are particularly appropriate for this use, as greater numbers of polymorphisms occur in the noncoding regions, making it easier to differentiate individuals using this technique. Examples of polynucleotide reagents include the nucleic acid molecules or the invention, or portions thereof, e.g., fragments having a length of at least 20 bases, preferably at least 30 bases.

The nucleic acid molecules described herein can further be used to provide polynucleotide reagents, e.g., labeled or labelable probes which can be used in, or example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

In a similar fashion, these reagents, primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trails are used for prognostic (predictive) purposes to thereby treat an individual prophylactically. Accordingly, one aspect of the present invention relates to diagnostic assays for determining protein and/or nucleic acid expression as well as activity of proteins of the invention, in the context of a biological sample (e.g., blood, serum, cells, tissue) to thereby determine whether an individual is afflicted with a disease or disorder, or is at risk of developing a disorder, associated with aberrant expression or activity. The invention also provides for prognostic (or predictive) assays for determining whether an individual is at risk of developing a disorder associated with activity or expression of proteins or nucleic acids of the invention.

For example, mutations in a specified gene can be assayed in a biological sample. Such assays can be used for prognostic or predictive purpose to thereby phophylactically treat an individual prior to the onset of a disorder characterized by or associated with expression or activity of nucleic acid molecules or proteins of the invention.

Another aspect of the invention pertains to monitoring the influence of agents (e.g., drugs, compounds) on the expression or activity of proteins of the invention in clinical trials.

These and other agents are described in further detail in the following sections.

1. Diagnostic Assays

An exemplary method for detecting the presence or absence of proteins or nucleic acids of the invention in a biological sample involves obtaining a biological sample from a test subject and contacting the biological sample with a compound or an agent capable of detecting the protein, or nucleic acid (e.g., mRNA, genomic DNA) that encodes the protein, such that the presence of the protein or nucleic acid is detected in the biological sample. A preferred agent for detecting mRNA or genomic DNA is a labeled nucleic acid probe capable of hybridizing to mRNA or genomic DNA sequences described herein. The nucleic acid probe can be, for example, a full-length nucleic acid, or a portion thereof, such as an oligonucleotide of at least 15, 30, 50, 100, 250 or 500 nucleotides in length and sufficient to specifically hybridize under stringent conditions to appropriate mRNA or genomic DNA. For example, the nucleic acid probe can be all or a portion of SEQ ID NOS: 1–5, or the complement of SEQ ID NOS: 1–5, or a portion thereof. Other suitable probes for use in the diagnostic assays of the invention are described herein.

A preferred agent for detecting proteins of the invention is an antibody capable of binding to the protein, preferably an antibody with a detectable label. Antibodies can be polyclonal, or more preferably, monoclonal. An intact antibody, or a fragment thereof (e.g., Fab or $F(ab^1)_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, calls and biological fluids isolated from a subject, as well as tissues, cells and fluids present within a subject. That is, the detection method of the invention can be used to detect mRNA, protein, or genomic DNA of the invention in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled anti-protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample or biopsy isolated by conventional means from a subject.

In another embodiment, the methods further involve obtaining a control biological sample from a control subject, contacting the control sample with a compound or agent capable of detecting protein, mRNA, or genomic DNA of the invention, such that the presence of protein, mRNA or genomic DNA is detected in the biological sample, and comparing the presence of protein, mRNA or genomic DNA in the control sample with the presence of protein, mRNA or genomic DNA in the test sample.

The invention also encompasses kits for detecting the presence of proteins or nucleic acid molecules of the invention in a biological sample. For example, the kit can comprise a labeled compound or agent capable of detecting protein or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid.

2. Prognostic Assays

The diagnostic methods described herein can furthermore be utilized to identify subjects having or at risk of developing a disease or disorder associated with aberrant expression or activity of proteins and nucleic acid molecules of the invention. For example, the assays described herein, such as the preceding diagnostic assays or the following assays can be utilized to identify a subject having or at risk of developing a disorder associated with protein or nucleic acid expression or activity such as a proliferative disorder, a differentiative or developmental disorder, or a hematopoietic disorder. Alternatively, the prognostic assays can be utilized to identify a subject having or at risk for developing a differentiative or proliferative disease, particularly of the brain. Thus, the present invention provides a method for identifying a disease or disorder associated with aberrant expression or activity of proteins or nucleic acid molecules of the invention, in which a test sample is obtained from a subject and protein or nucleic acid (e.g., mRNA, genomic DNA) is detected, wherein the presence of protein or nucleic acid is diagnostic for a subject having or at risk of developing a disease or disorder associated with aberrant expression or activity of the protein or nucleic acid sequence of the invention. As used herein, a "test sample" refers to a biological sample obtained from a subject of interest. For example, a test sample can be a biological fluid (e.g., serum), cell sample, or tissue (e.g., brain tissue).

Furthermore, the prognostic assays described herein can be used to determine whether a subject can be administered an agent (e.g., an agonist, antagonist, peptidomimetic, protein, polypeptide, nucleic acid, small molecule, or other drug candidate) to treat a disease or disorder associated with aberrant expression or activity of a protein or nucleic acid molecule of the invention. For example, such methods can be used to determine whether a subject can be effectively treated with an agent for a disorder, such as a proliferative disorder, a differentiative or developmental disorder, or a hematopoietic disorder. Alternatively, such methods can be used to determine whether a subject can be effectively treated with an agent for a differentiative or proliferative disease (e.g., cancer). Thus, the present invention provides methods for determining whether a subject can be effectively treated with an agent for a disorder associated with aberrant expression or activity of a protein or nucleic acid of the present invention, in which a test sample is obtained and protein or nucleic acid expression or activity is detected (e.g., wherein the abundance of particular protein or nucleic acid expression or activity is diagnostic for a subject that can be administered the agent to treat a disorder associated with aberrant expression or activity.)

The methods of the invention can also be used to detect genetic alterations in genes or nucleic acid molecules of the present invention, thereby determining if a subject with the altered gene is at risk for a disorder characterized by aberrant development, aberrant cellular differentiation, aberrant cellular proliferation or an aberrant hematopoietic response. In preferred embodiments, the methods include detecting, in a sample of cells from the subject, the presence or absence of a genetic alteration characterized by at least one of an alteration affecting the integrity of a gene encoding a particular protein, or the mis-expression of the gene. For example, such genetic alterations can be detected by ascertaining the existence of at least one of (1) a deletion of one or more nucleotides; (2) an addition of one or more nucleotides; (3) a substitution of one or more nucleotides, (4) a chromosomal rearrangement; (5) an alteration in the level of a messenger RNA transcript; (6) aberrant modification, such as of the methylation pattern of the genomic DNA; (7) the presence of a non-wild type splicing pattern of a messenger RNA transcript; (8) a non-wild type level; (9) allelic loss; and (10) inappropriate post-translational modification. As described herein, there are a large number of assay techniques known in the art which can be used for detecting alterations in a particular gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such an anchor PCR or RACE PCR, or, alternatively, in a ligation chain reaction (LCR) (see, e.g., Landegran et al. (1988) *Science*, 241:1077–1080; and Nakazawa et al. (1994) *PNAS*, 91:360–364), the latter of which can be particularly useful for detecting point mutations (see Abravaya et al. (1995) *Nucleic Acids Res.*, 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA*, 87:1874–1878), transcriptional amplification system (Kwoh, D. Y. et al., (1989) *Proc. Natl. Acad. Sci. USA*, 86:1173–1177), Q-Beta Replicase (Lizardi, P. M. et al., (1988) *Bio/Technology*, 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a given gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for sample, U.S. Pat. No. 5,498,531) ca be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotide probes (Cronin, M. T. et al. (1996) Human Mutation, 7:244–255; Kozal, M. J. et al. (1996) *Nature Medicine*, 2:753–759). For example, genetic mutations can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the gene and detect mutations by comparing the sequence of the gene from the sample with the corresponding wild-type (control) gene sequence. Examples of sequencing reactions include those based on techniques developed by Maxim and Gilbert ((1997) PNAS, 74:560) or Sanger ((1977) *PNAS,* 74:5463). It is also contemplated that any of a variety of automated sequencing procedures can be utilized when performing the diagnostic assays ((1995) *Biotechniques,* 19:448), including sequencing by mass spectrometry (see, e.g., PCT International Publication No. WO 94/16101; Cohen et al. (1996) *Adv. Chromatogr.*, 36:127–162; and Griffin et al. (1993) *Appl. Biochem. Biotechnol.*, 38:147–159).

Other methods for detecting mutations include methods in which protection from cleavage agents is used to detect mismatched bases in RNA/RNA or RNA/DNA heteroduplexes (Myers et al. (1985) *Science,* 230:1242). In general, the art technique of "mismatch cleavage" starts by providing heteroduplexes of formed by hybridizing (labeled) RNA or DNA containing the wild-type sequence with potentially mutant RNA or DNA obtained from a tissue sample. The double-standard duplexes are treated with an agent which cleaves single-stranded regions of the duplex such as which will exist due to base pair mismatches between the control and sample strands. For instance, RNA/DNA duplexes can be treated with Rnase and DNA/DNA hybrids treated with S1 nuclease to enzymatically digest the mismatched regions. After digestion of the mismatched regions, the resulting material is then separated by size on denaturing polyacrylamide gels to determine the site of mutation. See, for example Cotton et al. (1988) *Proc. Natl. Acad. Sci. USA,* 85:4397; Saleeba et al. (1992) *Methods Enzymol.,* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair", enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis,* 15:1657–1662). According to an exemplary embodiment, a probe based on an nucleotide sequence of the invention is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) Proc. Natl. Acad. Sci. USA, 86:2766, see also Cotton (1993) Mutat Res, 285:125–144; and Hayashi (1992) Genet Anal. Tech. Appl., 9:73–79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet., 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature, 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem., 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature, 324:163); Saiki et al. (1989) Proc. Natl. Acad. Sci. USA, 86:6320). Such allele-specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res., 17:2437–2448) or at the extreme 3' end of one primer where, under appropriate conditions, mismatch can prevent, or reduce polymerase extension (Prossner (1993) Tibtech, 11:238). In addition it may be desirable to introduce a novel restriction site in the region of the mutation to create cleavage-based detection (Gasparini et al. (1992) Mol. Cell Probes, 6:1). It is anticipated that in certain embodiments amplification may also be performed using Taq ligase for amplification (Barany (1991) Proc. Natl. Acad. Sci. USA, 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene of the present invention. Any cell type or tissue in which the gene is expressed may be utilized in the prognostic assays described herein.

3. Monitoring of Effects During Clinical Trials

Monitoring the influence of agents (e.g., drugs, compounds) on the expression or activity of nucleic acid molecules or proteins of the present invention (e.g., modulation of cellular signal transduction, regulation of gene transcription in a cell involved in development or differentiation, regulation of cellular proliferation) can be applied not only in basic drug screening, but also in clinical trials. For example, the effectiveness of an agent determined by a screening assay as described herein to increase gene expression, protein levels, or upregulate protein activity, can be monitored in clinical trails of subjects exhibiting decreased gene expression, protein levels, or downregulated protein activity. Alternatively, the effectiveness of an agent determined by a screening assay to decrease gene expression, protein levels, or downregulate protein activity, can be monitored in clinical trials of subjects exhibiting increased gene expression, protein levels, or upregulated protein activity. In such clinical trials, the expression or activity of the specified gene and, preferably, other genes that have been implicated in, for example, a proliferative disorder can be used as a "read out" or markers of the phenotype of a particular cell.

For example, and not by way of limitation, genes that are modulated in cells by treatment with an agent (e.g., compound, drug or small molecule) which modulates protein activity (e.g., identified in a screening assay as described herein) can be identified. Thus, to study the effect of agents on proliferative disorders, developmental or differentiative disorder, or hematopoietic disorder, for example, in a clinical trial, cells can be isolated and RNA prepared and analyzed for the levels of expression of the specified gene and other genes implicated in the proliferative disorder, developmental or differentiative disorder, or hematopoietic disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of the specified gene or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, polypeptide, nucleic acid, small molecule, or other drug candidate identified by the screening assays described herein) comprising the steps of (I) obtaining a pre-administration sample from a subject prior to administration of the agent; (ii) detecting the level of expression of a specified protein, mRNA, or genomic DNA of the invention in the pre-administration sample; (iii) obtaining one or more post-administration samples from the subject; (iv) detecting the level of expression or activity of the protein, mRNA, or genomic DNA in the post-administration samples; (v) comparing the level of expression or activity of the protein, mRNA, or genomic DNA in the pre-administration sample with the protein, mRNA, or genomic DNA in the post-administration sample or samples; and (vi) altering the administration of the agent to the subject accordingly. For example, increased administration of the agent may be desirable to increase the expression or activity of the protein or nucleic acid molecule to higher levels than detected, i.e., to increase effectiveness of the agent. Alternatively, decreased administration of the agent may be desirable to decrease effectiveness of the agent. According to such an embodiment, protein or nucleic acid expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder or having a disorder associated with aberrant expression or activity of proteins or nucleic acids of the invention. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with the molecules of the present invention or modulators according to that individual's drug response genotype. Pharmacogenomics allows a clinician or physician to target prophylactic or therapeutic treatments to patients who will most benefit from the treatment and to avoid treatment of patients who will experience toxic drug related side effects.

1. Prophylactic Methods

In one aspect, the invention provides a method for preventing in a subject, a disease or condition associated with aberrant expression or activity of genes or proteins of the present invention, by administering to the subject an agent which modulates expression or at least one activity of a gene or protein of the invention. Subjects at risk for a disease which is caused or contributed to by aberrant gene expression or protein activity can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating expression or activity of genes or proteins of the invention for therapeutic purposes. The modulatory method of the invention involves contacting a cell with an agent that modulates one or more of the activities of the specified protein associated with the cell. An agent that modulates protein activity can be an agent as described herein, such as a nucleic acid or a protein, a naturally-occurring target molecule of a protein described herein, a polypeptide, a peptidomimetic, or other small molecule. In one embodiment, the agent stimulates one or more protein activities. Examples of such stimulatory agents include active protein as well as a nucleic acid molecule encoding the protein that has been introduced into the cell. In another embodiment, the agent inhibits one or more protein activities. Examples of such inhibitory agents include antisense nucleic acid molecules and anti-protein antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a protein or nucleic acid molecule of the invention. In one embodiment, the method involves administering an agent (e.g., an agent identified by a screening assay described herein), or combination of agents that modulates (e.g., upregulates or downregulates) expression or activity of a gene or protein of the invention. In another embodiment, the method involves administering a protein or nucleic acid molecule of the invention as therapy to compensate for reduced or aberrant expression or activity of the protein or nucleic acid molecule.

Stimulation of protein activity is desirable in situations in which the protein is abnormally downregulated and/or in which increased protein activity is likely to have a beneficial effect. Likewise, inhibition of protein activity is desirable in situations in which the protein is abnormally upregulated and/or in which decreased protein activity is likely to have a beneficial effect. One example of such a situation is where a subject has a disorder characterized by aberrant development or cellular differentiation. Another example of such a situation is where the subject has a proliferative disease (e.g., cancer) or a disorder characterized by an aberrant hematopoietic response. Yet another example of such a situation is where it is desirable to achieve tissue regeneration in a subject (e.g., where a subject has undergone brain or spinal cord injury and it is desirable to regenerate neuronal tissue in a regulated manner).

3. Pharmacogenomics

The molecules of the present invention, as well as agents, or modulators which have a stimulatory or inhibitory effect on the protein activity (e.g., gene expression) as identified by a screening assay described herein can be administered to individuals to treat (prophylactically or therapeutically) disorders (e.g., proliferative or developmental disorders) associated with aberrant protein activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a molecule of the invention or modulator thereof, as well as tailoring the dosage and/or therapeutic regimen of treatment with such a molecule or modulator.

Pharmacogenomics deals with clinically significant hereditary variations in the response to drugs due to altered drug disposition and abnormal action in affected persons. See e.g., Eichelbaum, M., *Clin Exp Pharmacol. Physiol.,* (1996) 23(10–11):983–985 and Linder, M. W., *Clin. Chem.* (1997) 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1,000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a protein or a receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2(NAT 2) and cytochrme P450 enzymes CYP2D6 and CYP2C19) has provided an explanation as to why some patients do not obtain the expected drug effects or show exaggerated drug response and serious toxicity afer taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a molecule or modulator of the present invention) can given an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a molecule or modulator of the invention, such as a modulator identified by one of the exemplary screening assays described herein.

The contents of all references, patents and published patent applications cited throughout this application are hereby incorporated by reference.

EXAMPLES

CDNA Library Construction

RNA was isolated from a mouse brain tissue library or from a mouse hypothalamus tissue library by the guanidinium isothiocyanate/cesium chloride density gradient method (modified from Chirgwin et al., *Biochemistry* 18(24): 5294–5299 (1997) and Sambrook, supra) . The total RNA was incubated with Dnase to remove mitochondria DNA contamination. PolyA+ RNA was purified by Oligotex mRNA mini kit (Qiagen Corporation, Studio City, Calif.). One microgram of purified polyA+ RNA was used for cDNA synthesis. First and second strand cDNA synthesis and cDNA fractionation were done using the Gibco/BRL kit "Superscript Plasmid System for cDNA Synthesis and Plasmid Cloning" (Gibco/BRL, Gaithersburg, Md.). cDNA representing the largest fractions were ligated into lambda vector ZIPLOX (Gibco/BRL, Gaithersburg, Md.), packaged using the Stratagene III Gold packaging kit (Stratagene, La Hoya, Calif.).

FIG. 1 shows the nucleotide sequences (SEQ ID NOS: -4,respectively) of nucleic acid molecules identified by this method. SEQ ID NO: 1 was derived from the mouse brain library; SEQ ID NO: 3 was derived from the mouse hypothalamus library. SEQ ID NOS: 2 and 4 are edited versions of SEQ ID NOS: 1 and 3, respectively, which were edited to facilitate assembly of a contiguous sequence.

FIG. 2 shows the nucleotide sequence (SEQ ID NO: 5) of a contiguous nucleotide sequence assembled from edited versions of SEQ ID NOS: 1 and 3. Nucleotides 1–350 were derived from SEQ ID NO: 1, and nucleotides 131–428 were derived from SEQ ID NO: 3.

EQUIVALENTS

While this invention has been particularly shown and described with reference to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An isolated nucleic acid molecule comprising a nucleotide sequence selected from the group consisting of:
    a) SEQ ID NO: 1; and
    b) the complement of SEQ ID NO: 1.

2. An isolated nucleic acid molecule according to claim 1, which is expressed in cells of the brain.

3. An isolated nucleic acid molecule according to claim 1 which is DNA.

4. An isolated nucleic acid molecule according to claim 1 which is RNA.

5. An isolated nucleic acid molecule consisting of a nucleotide sequence selected from the group consisting of:
    a) SEQ ID NO: 1; and
    b) the complement of SEQ ID NO: 1.

6. An isolated portion of a nucleic acid molecule consisting of a nucleotide sequence selected from the group consisting of:
    a) SEQ ID NO: 1; and
    b) the complement of SEQ ID NO: 1,
wherein the portion is at least about 10 nucleotides in length.

7. An isolated portion of a nucleic acid molecule consisting of a nucleotide sequence selected from the group consisting of:
    a) SEQ ID NO: 1; and
    b) the complement of SEQ ID NO: 1,
wherein the portion is at least 20 nucleotides in length.

8. A DNA construct comprising the isolated nucleic acid molecule of claim 1 operatively linked to a regulatory sequence.

9. A DNA construct comprising the isolated nucleic acid molecule of claim 5 operatively linked to a regulatory sequence.

10. A recombinant host cell comprising the isolated nucleic acid molecule of claim 1 operatively linked to a regulatory sequence.

11. A recombinant host cell comprising the isolated nucleic acid molecule of claim 5 operatively linked to a regulatory sequence.

12. The recombinant host cell of claim 10 wherein said cell is selected from the group consisting of bacterial cells, fungal cells, plant cells, insect cells and mammalian cells.

13. The recombinant host cell of claim 11 wherein said cell is selected from the group consisting of bacterial cells, fungal cells, plant cells, insect cells and mammalian cells.

14. A method for assaying the presence of a nucleic acid molecule in a sample, comprising contacting said sample with a nucleotide sequence selected from the group consisting of:

a) SEQ ID NO: 1;
    b) the complement of SEQ ID NO: 1;
    c) a portion of SEQ ID NO: 1 which is at least 10 nucleotides in length; and
    d) a portion of the complement of SEQ ID NO: 1 which is at least 10 nucleotides in length under conditions appropriate for specific hybridization.

15. A nucleic acid molecule comprising a nucleotide sequence which is greater than about 75 percent identical to a nucleotide sequence selected from the group consisting of:

a) SEQ ID NO: 1; and
    b) the complement of SEQ ID NO: 1.

16. A nucleic acid molecule which hybridizes under high stringency conditions to a nucleotide sequence selected from the group consisting of:

a) SEQ ID NO: 1; and
    b) the complement of SEQ ID NO: 1.

* * * * *

UNITED STATES PATENT AND TRADEMARK OFFICE
CERTIFICATE OF CORRECTION

PATENT NO. : 5,969,123
DATED : October 19, 1999
INVENTOR(S) : Douglas A. Holtzman It is certified that error appears in the above-identified patent and that said Letters Patent is hereby corrected as shown below:

Please cancel Claims 6, 7, 15 and 16.

Signed and Sealed this

Twenty-fifth Day of July, 2000

Attest:

Q. TODD DICKINSON

*Attesting Officer*     *Director of Patents and Trademarks*